United States Patent
Nagae et al.

(10) Patent No.: US 10,254,228 B2
(45) Date of Patent: Apr. 9, 2019

(54) DETECTION CHIP AND DETECTION METHOD

(71) Applicant: Konica Minolta, Inc., Tokyo (JP)

(72) Inventors: Kosuke Nagae, Tokyo (JP); Takatoshi Kaya, Tokyo (JP); Yukito Nakamura, Saitama (JP)

(73) Assignee: Konica Minolta, Inc., Tokyo (JP)

( * ) Notice: Subject to any disclaimer, the term of this patent is extended or adjusted under 35 U.S.C. 154(b) by 35 days.

(21) Appl. No.: 15/534,797

(22) PCT Filed: Nov. 20, 2015

(86) PCT No.: PCT/JP2015/082682
§ 371 (c)(1),
(2) Date: Jun. 9, 2017

(87) PCT Pub. No.: WO2016/093039
PCT Pub. Date: Jun. 16, 2016

(65) Prior Publication Data
US 2018/0266954 A1    Sep. 20, 2018

(30) Foreign Application Priority Data
Dec. 9, 2014   (JP) ................. 2014-249044

(51) Int. Cl.
*G01N 21/55*   (2014.01)
*G01N 21/64*   (2006.01)
*G01N 21/552*  (2014.01)

(52) U.S. Cl.
CPC ......... *G01N 21/648* (2013.01); *G01N 21/553* (2013.01); *G01N 21/64* (2013.01)

(58) Field of Classification Search
CPC .... G01N 21/553; G01N 21/55; G01N 21/554; G01N 21/474; G01N 21/57
(Continued)

(56) References Cited

U.S. PATENT DOCUMENTS 4,259,682 A * 3/1981 Gamo ............... H01L 21/78
                                                148/DIG. 28
8,805,536 B2 * 8/2014 Li ..................... H01R 43/16
                                                607/116
(Continued)

FOREIGN PATENT DOCUMENTS

JP    10-307141 A    11/1998
JP    2001-337036 A  12/2001
(Continued)

OTHER PUBLICATIONS

International Patent Application No. PCT/JP2015/082682; Int'l Written Opinion; dated Feb. 16, 2016; 6 pages.
(Continued)

*Primary Examiner* — Md M Rahman
(74) *Attorney, Agent, or Firm* — Baker & Hostetler LLP

(57) ABSTRACT

The detection chip according to the present invention has an accommodating part, a metal film, a first reaction field, and a second reaction field. The accommodating part accommodates a liquid. The metal film is arranged in a bottom part of the accommodating part so that one face thereof faces into the accommodating part. The first reaction field and the second reaction field are arranged in mutually different regions on one face of the metal film. A capture body is immobilized in the first reaction field and the second reaction field. When the liquid is accommodated in the accommodating part, the depth of the liquid on the first reaction field differs from the depth of the liquid on the second reaction field.

15 Claims, 8 Drawing Sheets

(58) Field of Classification Search
USPC .......................................................... 356/445
See application file for complete search history.

(56) References Cited

U.S. PATENT DOCUMENTS

| | | | |
|---|---|---|---|
| 2002/0151040 A1* | 10/2002 | O' Keefe | B01F 13/0084 435/287.2 |
| 2007/0006625 A1* | 1/2007 | Reinschke | B21B 37/28 72/11.7 |
| 2008/0218761 A1 | 9/2008 | Nishikawa et al. | |
| 2008/0246961 A1 | 10/2008 | Zhang et al. | |
| 2011/0053794 A1* | 3/2011 | Zhang | B01J 19/0046 506/9 |
| 2011/0143466 A1* | 6/2011 | Chen | H01L 21/0242 438/29 |
| 2011/0238152 A1* | 9/2011 | Richter | A61F 2/915 623/1.15 |
| 2012/0170032 A1* | 7/2012 | Zhu | G01N 21/658 356/301 |
| 2012/0170033 A1* | 7/2012 | Zhu | G01N 21/658 356/301 |
| 2013/0264307 A1* | 10/2013 | Lin | C01B 31/0438 216/49 |
| 2014/0030151 A1* | 1/2014 | Horii | G06F 1/206 422/69 |
| 2014/0074200 A1* | 3/2014 | Li | H01R 43/16 607/116 |
| 2014/0128588 A1* | 5/2014 | Hargreaves | C12N 15/115 536/23.1 |
| 2015/0124254 A1* | 5/2015 | Page | G01N 21/553 356/369 |
| 2015/0233832 A1* | 8/2015 | Maruyama | G01N 21/658 356/244 |
| 2015/0253596 A1* | 9/2015 | Zhang | G02F 1/1309 349/158 |
| 2016/0061993 A1* | 3/2016 | Ren | G02B 1/002 349/62 |
| 2016/0064612 A1* | 3/2016 | Ren | H01L 33/38 349/62 |
| 2016/0139511 A1* | 5/2016 | Li | H01J 37/32009 216/48 |
| 2016/0299047 A1* | 10/2016 | Molla | B01L 3/502784 |
| 2016/0329184 A1* | 11/2016 | Wei | H01J 1/14 |
| 2017/0123276 A1* | 5/2017 | Um | G02F 1/133345 |

FOREIGN PATENT DOCUMENTS

| | | |
|---|---|---|
| JP | 2003-121349 A | 4/2003 |
| JP | 2005-291966 A | 10/2005 |
| JP | 2008-216055 A | 9/2008 |
| JP | 2011-158369 A | 8/2011 |
| WO | WO 2010/134470 A1 | 11/2010 |

OTHER PUBLICATIONS

European Patent Application No. 15868386.2; Extended Search Report; dated Feb. 21, 2018; 7 pages.
International Patent Application No. PCT/JP2015/082682; Int'l Preliminary Report on Patentability; dated Jun. 22, 2017; 8 pages.

* cited by examiner

DETECTION CHIP AND DETECTION METHOD

TECHNICAL FIELD

The present invention relates to a detection chip for use in detecting an analyte utilizing surface plasmon resonance, and a detection method using the detection chip.

BACKGROUND ART

In a clinical test or the like, highly sensitive and quantitative detection of a trace amount of analyte, such as a protein or DNA, would allow a quick understanding of a patient's condition and the subsequent his/her treatment. For this reason, there is a need for a method of detecting a trace amount of analyte highly sensitively and quantitatively.

As a highly sensitive method of detecting an analyte, surface plasmon-field enhanced fluorescence spectroscopy (hereinafter abbreviated as "SPFS") is known. SPFS utilizes surface plasmon resonance (hereinafter abbreviated as "SPR") generated by irradiating a metal film with light under specific conditions (see, Patent Literature (hereinafter abbreviated as PTL) 1, for example).

In SPFS, a ligand (e.g., primary antibody) that can specifically bind to an analyte is first immobilized above a metal film, thereby forming a reaction site for specifically capturing an analyte. When a sample containing an analyte is provided to the reaction site, the analyte binds to the ligand in the reaction site. Then, when another ligand (e.g., secondary antibody) labeled with a fluorescent substance is provided to the reaction site, the analyte bound to the ligand in the reaction site is labeled with the fluorescent substance. When the metal film is irradiated with excitation light in this state, the fluorescent substance that labels the analyte is excited by enhanced electric fields due to SPR to emit fluorescence. Thus, the detection of emitted fluorescence allows the detection of the presence or an amount of the analyte. SPFS can detect an analyte highly sensitively since a fluorescent substance is excited by enhanced electric fields due to SPR.

During the detection of fluorescence, however, the presence of an unreacted fluorescent substance that does not label an analyte above a metal film results in background noise. Accordingly, in order to detect an analyte accurately, it is preferable to remove an unreacted fluorescent substance in advance by washing.

SPFS is broadly categorized into prism coupling (PC)-SPFS and grating coupling (GC)-SPFS in accordance with a means for coupling excitation light with surface plasmon. PC-SPFS utilizes a prism formed on one surface of a metal film. In this method, excitation light and surface plasmon are coupled by total reflection of excitation light at an interface between the prism and the metal film. Although PC-SPFS is a mainstream method today, it has a challenge in downsizing a detection apparatus since a prism is used and an incident angle of excitation light on a metal film is large.

In contrast, GC-SPFS couples excitation light with surface plasmon utilizing a diffraction grating (see PTL 2, for example). GC-SPFS can downsize a detection apparatus compared with PC-SPFS, since a prism is not used and an incident angle of excitation light on a diffraction grating is small.

CITATION LIST

Patent Literature

PTL 1
Japanese Patent Application Laid-Open No. 10-307141

PTL 2
Japanese Patent Application Laid-Open No. 2011-158369

SUMMARY OF INVENTION

Technical Problem

As described above, although GC-SPFS has the advantage that a detection apparatus can be downsized compared with PC-SPFS, GC-SPFS has not yet been vigorously studied compared with PC-SPFS. Accordingly, a detection apparatus and a detection method utilizing GC-SPFS have room for improvement in detection sensitivity.

In addition, both GC-SPFS and PC-SPFS may fail to detect an analyte accurately due to the effect of background noise caused by an unreacted fluorescent substance. When washing is performed to eliminate the effect of background noise, there is a problem in which a binding state between an analyte and a metal film (or primary antibody) varies during washing, and thus a real-time measurement of a reaction process is impossible.

An object of the present invention is to provide a detection chip for use in detecting the presence or an amount of an analyte accurately utilizing SPFS even if an unreacted fluorescent substance is present above a metal film, as well as a detection method using the detection chip.

Solution to Problem

To achieve at least one of the aforementioned objects, a detection chip according to an embodiment of the present invention includes: a housing section for housing a liquid; a metal film disposed in a bottom portion of the housing section so that one surface of the metal film faces inside the housing section; a first reaction site where a ligand for capturing an analyte is immobilized, the first reaction site being disposed on the one surface of the metal film; and a second reaction site where the ligand is immobilized, the second reaction site being disposed in a different region from the first reaction site on the one surface of the metal film, in which when a liquid is housed inside the housing section, a depth of the liquid above the first reaction site is different from a depth of the liquid above the second reaction site.

To achieve at least one of the aforementioned objects, a detection method according to an embodiment of the present invention for detecting an analyte utilizing surface plasmon resonance, includes: a first step of binding an analyte labeled with a fluorescent substance to the ligand in the first reaction site and in the second reaction site inside a housing section of the detection chip according to the present invention; a second step of irradiating the metal film positioned under the first reaction site with excitation light so as to generate surface plasmon resonance while the liquid is present inside the housing section in a first depth of the liquid above the first reaction site, and detecting fluorescence emitted from the fluorescent substance present above the first reaction site; a third step of irradiating the metal film positioned under the second reaction site with excitation light so as to generate surface plasmon resonance while the liquid is present inside the housing section in a second depth different from the first depth of the liquid above the second reaction site, and detecting fluorescence emitted from the fluorescent substance present above the second reaction site; and a fourth step of calculating a signal value indicating the presence or an amount of an analyte based on a detected value obtained in each of the second step and the third step.

Advantageous Effects of Invention

According to the present invention, a detection chip and a detection method for detecting an analyte utilizing SPFS can accurately and easily detect an analyte. Moreover, according to the present invention, an analyte can be detected in real time.

DESCRIPTION OF EMBODIMENTS

Embodiments of the present invention will be described in detail hereinafter with reference to the accompanying drawings.

[Embodiment 1]

(Configuration of Detection Chip)

Figure 1A:
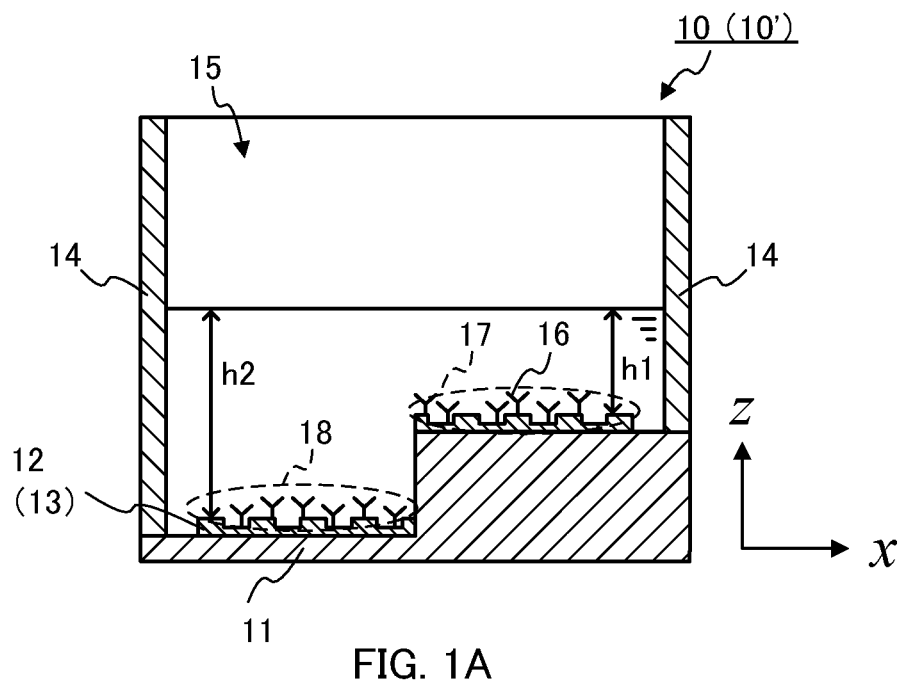
FIG. 1A is a sectional view illustrating a configuration of a detection chip according to Embodiments 1 and 2.
Figure 1B:
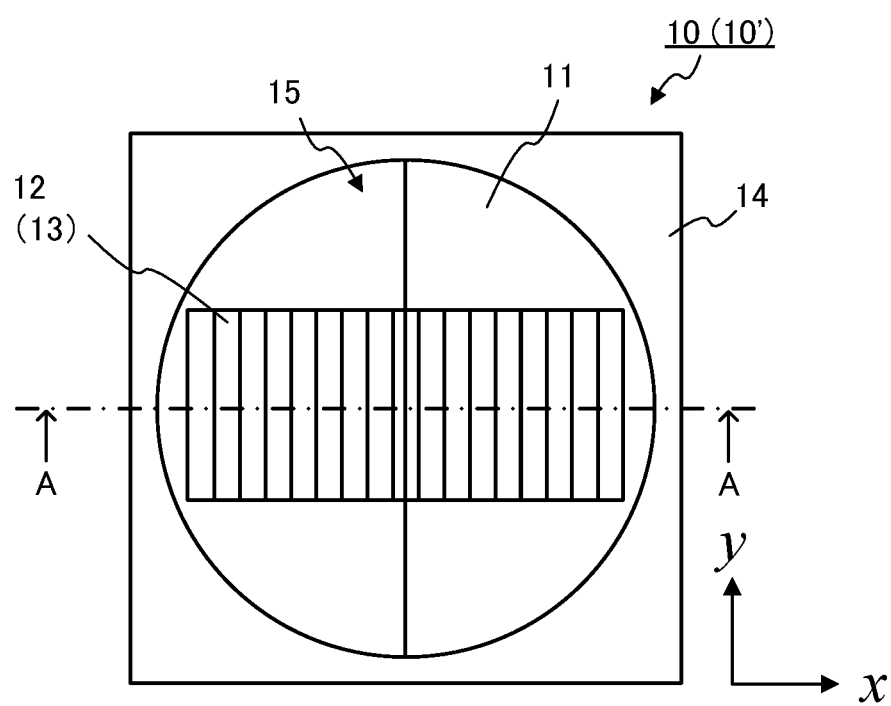
FIG. 1B is a plan view of a detection chip according to Embodiments 1 and 2.
Figure 2:
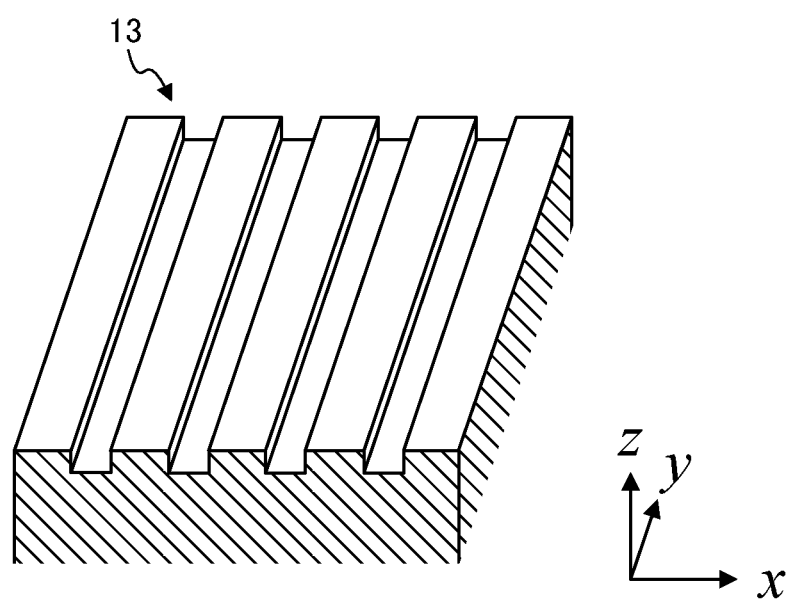
FIG. 2 is a perspective view of a diffraction grating of a detection chip according to Embodiments 1 and 2.

FIG. 1A is a sectional view of detection chip 10 according to an embodiment, and FIG. 1B is a plan view of detection chip 10. The sectional view of FIG. 1A corresponds to a sectional view at the A-A line in FIG. 1B. FIG. 2 is a perspective view of diffraction grating 13 of detection chip 10 according to the embodiment. As illustrated in FIGS. 1A, 1B, and 2, a height direction of detection chip 10 is defined as z-direction, an alignment direction of a periodic structure of diffraction grating 13 as x-direction, and a perpendicular direction to both z-direction and x-direction as y-direction.

As illustrated in FIGS. 1A and 1B, detection chip 10 includes substrate 11, metal film 12 formed on substrate 11, and frame 14 disposed on substrate 11. Housing section 15 for housing a liquid is formed by disposing frame 14 on substrate 11. Although details will be described hereinafter, detection chip 10 according to the embodiment houses a liquid in different depths (first depth h1 and second depth h2) when the liquid is housed inside housing section 15. Metal film 12 includes diffraction grating 13, and ligand 16 (e.g., primary antibody) is immobilized on diffraction grating 13. Thus, a surface of diffraction grating 13 also functions as a reaction site for binding ligand 16 and an analyte.

Substrate 11 is a support member for metal film 12. The shape of substrate 11 is not limited. In the embodiment, substrate 11 has one step, and thus two terrace surfaces are formed on substrate 11. The orientation and the height of the step are not limited as long as the optical paths of excitation light α and fluorescence β are not obstructed. For example, a wall surface of the step may be parallel to yz-plane or parallel to xz-plane. Materials for substrate 11 are not limited as long as they have enough mechanical strength to support metal film 12. Examples of the materials for substrate 11 include inorganic materials, such as glass, quartz, and silicon, and resins, such as an acrylic resin, polymethyl methacrylate, a polycarbonate, polystyrene, and a polyolefin.

Metal film 12 is disposed on a bottom portion of housing section 15 with one surface faced inside housing section 15. In the embodiment, metal film 12 is disposed on substrate 11 so as to be exposed to inside housing section 15 both on a terrace surface on the upper side and on a terrace surface on the lower side. As already mentioned, metal film 12 includes diffraction grating 13. Because of this, surface plasmon, which is generated in metal film 12 upon irradiation of metal film 12 with light at a specific incident angle, and evanescent waves, which are generated by diffraction grating 13, are coupled, thereby generating surface plasmon resonance (SPR). The thickness of metal film 12 is not limited. The thickness of metal film 12 is, for example, 30 to 500 nm, preferably 100 to 300 nm. Materials for metal film 12 are not limited as long as metals can generate surface plasmon. Examples of the materials for metal film 12 include gold, silver, aluminum, platinum, copper, and an alloy thereof.

Diffraction grating 13 generates evanescent waves when metal film 12 is irradiated with light. The shape of diffraction grating 13 is not limited as long as evanescent waves can be generated. For example, diffraction grating 13 may be a one-dimensional diffraction grating or a two-dimensional diffraction grating. As illustrated in FIG. 2, in the embodiment, diffraction grating 13 is a one-dimensional diffraction grating, and is formed on a surface of metal film 12 as a plurality of parallel protruded strips (and recessed strips) at a specific spacing. Also, the cross-sectional shape of diffraction grating 13 is not limited. Examples of the cross-sectional shapes of diffraction grating 13 include a square waveform, a sinusoidal waveform, and a sawtooth shape. In the embodiment, the cross-sectional shape of diffraction grating 13 is a square waveform. The optical axis of excitation light α described hereinafter is parallel to xz-plane. The pitch and the depth of grooves (recessed strips) of diffraction grating 13 are not limited as long as evanescent waves can be generated, and can be set appropriately in accordance with a wavelength of light to be irradiated with. For example, the pitch of the grooves of diffraction grating 13 is preferably in a range of 100 nm to 2,000 nm, and the depth of the grooves of diffraction grating 13 is preferably in a range of 10 nm to 1,000 nm.

Ligand 16 for capturing an analyte is immobilized above diffraction grating 13. A region where ligand 16 is immobilized above diffraction grating 13 (metal film 12) is herein particularly referred to as "a reaction site." Ligand 16 specifically binds to an analyte. Thus, an analyte is immobilized on metal film 12 (diffraction grating 13). In the embodiment, ligand 16 is almost evenly immobilized on both the terrace surfaces on the upper side and on the lower side. In the embodiment, as illustrated in FIG. 1A, when a liquid is housed in chamber section 15, first reaction site 17, above which the depth of the liquid is first depth h1, and second reaction site, above which the depth of the liquid is second depth h2, are disposed on one surface of metal film 12. Second reaction site 18 is disposed in a different region from first reaction site 17. First reaction site 17 is disposed on a terrace surface on the upper side, and second reaction site 18 is disposed in a terrace surface on the lower side. In first reaction site 17 and in second reaction site 18, a same type of ligand is immobilized in a same concentration.

The types of ligand 16 are not limited as long as analytes can be captured. For example, ligand 16 is an antibody (primary antibody) that can specifically bind to an analyte, a fragment thereof, an enzyme that can specifically bind to an analyte, or the like.

Figure 3A:
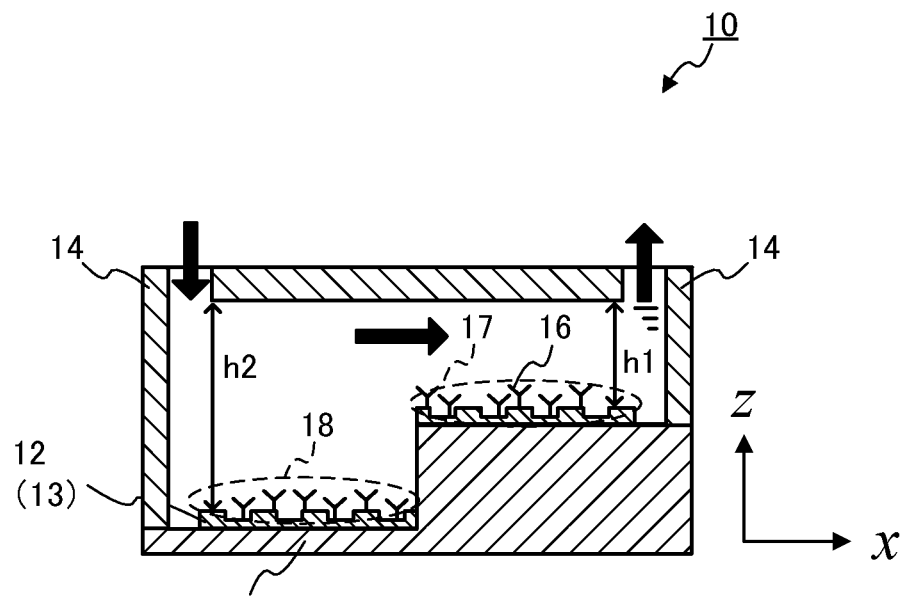
FIG. 3A and FIG. 3B are schematic sectional views illustrating other modes of a detection chip according to Embodiments 1 and 2.
Figure 3B:
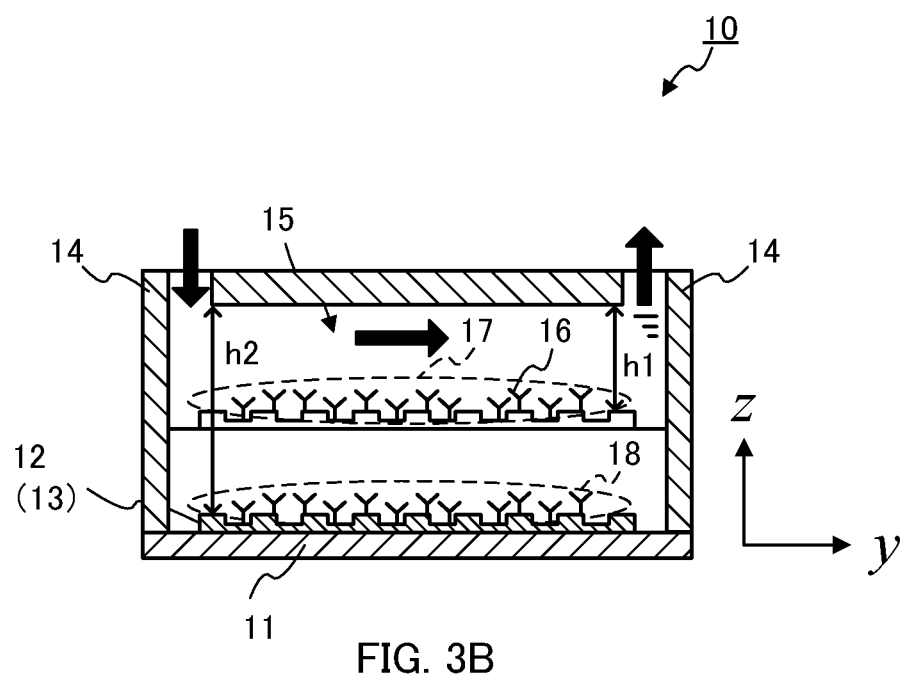

During use, diffraction grating 13 comes into contact with a liquid, such as a buffer, for reaction, washing, or other operations. Accordingly, diffraction grating 13 is typically disposed in space where a liquid can be housed. In the embodiment, diffraction grating 13 is disposed in a bottom portion of housing section 15. FIGS. 3A and 3B are schematic sectional views illustrating other modes of detection chip 10 according to the embodiment. As illustrated in FIGS. 1A and 1B, diffraction grating 13 may be disposed on an inner surface (e.g., bottom surface) of a well, which houses a liquid, or may be disposed on an inner surface (e.g., bottom surface) of a channel (flow cell), which can feed a liquid continuously, as illustrated in FIGS. 3A and 3B. For example, detection chip 10 illustrated in FIGS. 1A and 1B is suitable for a general measurement of an analyte (non-real-time measurement), as well as a mass transfer analysis (real-time measurement; see Embodiment 2) between the bulk and a surface of metal film 12, and a measurement of enhanced electric field space scale (z-axis direction). For example, detection chip 10 illustrated in FIGS. 3A and 3B is suitable for a general measurement of an analyte (non-real-time measurement) as well as a reaction constant analysis (real-time measurement; see Embodiment 2) of molecules (analyte) relative to another molecule (ligand) immobilized on a surface of metal film 12. In such a case, a step may be formed so that the wall surface is formed perpendicularly to the flow direction of a liquid inside the channel as illustrated in FIG. 3A, or formed along the flow direction of a liquid inside the channel as illustrated in FIG. 3B.

As illustrated in FIG. 1B, frame 14 is a plate having a through hole, and is disposed on substrate 11. Inner surfaces of the through hole constitute side surfaces of housing section 15. The thickness of frame 14 is not limited, and is set in accordance with a volume of liquid to be housed in housing section 15.

Housing section 15 is disposed on metal film 12 (or substrate 11), and houses a liquid. In the embodiment, as illustrated in FIG. 1A, housing section 15 includes a first bottom surface and a second bottom surface each disposed at a different height. The aforementioned first reaction site 17 is disposed on metal film 12 above the first bottom surface, and second reaction site 18 is disposed on metal film 12 above the second bottom surface. Housing section 15 can house a liquid in first depth h1 above first reaction site 17 (first bottom surface), and the liquid in second depth h2 above second reaction site 18 (second bottom surface). The depth of a liquid to be housed inside housing section 15 is not limited, but first depth h1 and second depth h2 are preferably in a range of 10 μm to 1 cm. When a ratio of second depth h2 to first depth h1 (h2/h1) is m, m is preferably in a range of 0.1 to 10 excluding 0.9 to 1.1. The shape, the size, or the like of housing section 15 is not limited as long as a desired volume of a liquid can be housed, and can be appropriately set in accordance with the use. As described above, housing section 15 is formed by disposing frame 14 on substrate 11, but a method for forming housing section 15 is not limited to this. Other examples of a method for forming housing section 15 include disposing a lid having recessed portions formed on the lower surface on substrate 11 (see FIGS. 3A and 3B, for example).

The type of liquid to be housed in housing section 15 is not limited. Examples of the types of liquid include a sample containing an analyte, a labeling solution containing a fluorescent substance, and a buffer. Generally, the refractive index and the dielectric constant of the liquid are comparable with the refractive index and the dielectric constant of water. The types of sample and analyte are not limited. Examples of the samples include bodily fluids, such as blood, serum, plasma, urine, nostril mucus, saliva, and semen, and a dilute solution thereof. Examples of the analytes include a nucleic acid (DNA, RNA, or the like), a protein (a polypeptide, an oligopeptide, or the like), an amino acid, a carbohydrate, a lipid, and a modified molecule thereof.

(Manufacturing Method of Detection Chip)

In the following, a manufacturing method of detection chip 10 according to the embodiment will be described. The manufacturing method of detection chip 10 is not limited. An example of the manufacturing method of detection chip 10 according to the embodiment will be described hereinafter.

Detection chip 10 according to the embodiment, for example, can be manufactured by performing 1) a first step of preparing frame 14 and substrate 11 in which a step and a plurality of grooves have been formed, 2) a second step of forming metal film 12 and reaction sites (first reaction site 17 and second reaction site 18) on substrate 11, and 3) a third step of mutually fixing frame 14 and substrate 11 in which the reaction sites have been formed. In the following, each step will be described.

In the first step, prepared are frame 14 and substrate 11 in which a step and a plurality of grooves have been formed. Specifically, a step and a plurality of grooves are formed on planar substrate 11 formed from a resin. A plurality of grooves constitute diffraction grating 13. A method for forming a step and grooves on substrate 11 is not limited, and can be appropriately selected from known methods. For example, a step may be formed on substrate 11 by molding or lithography. Also, grooves may be formed on substrate 11 by pressing with an uneven original plate.

In the second step, metal film 12 and reaction sites are formed on substrate 11. Specifically, metal film 12 may be formed in at least part of a region on substrate 11 where grooves have been formed, and a ligand may be immobilized on metal film 12. Thus, metal film 12 including diffraction grating 13 can be disposed on substrate 11. A formation method of metal film 12 is not limited. Examples of the formation method of metal film 12 include sputtering, vapor deposition, and plating.

Moreover, an immobilization method of ligand 16 is not limited. For example, a self-assembled monolayer (hereinafter referred to as "SAM") or a polymer film, to which ligand 16 is bound, may be formed on diffraction grating 13. Examples of SAM include films made of a substituted aliphatic thiol, such as $HOOC(CH_2)_{11}SH$. Examples of materials for the polymer film include polyethylene glycol and MPC polymer. Alternatively, a polymer having a reactive group (or a functional group that can be converted into a reactive group) that can bind to ligand 16 may be immobilized on diffraction grating 13, followed by binding of ligand 16 to the polymer.

The order of the formation of metal film 12 and the formation of diffraction grating 13 is not limited to the aforementioned method. For example, after forming metal film 12 on planar substrate 11, protruded/recessed shapes may be imparted to metal film 12.

In the third step, substrate 11 and frame 14 are fixed. A method for fixing frame 14 on substrate 11 is not limited. For example, examples of a method for fixing substrate 11 and frame 14 include bonding using a double-stick tape, an adhesive, or the like, laser welding, and ultrasonic welding.

Through the above procedure, detection chip 10 according to the embodiment can be manufactured. The order of performing the second step and the third step is not limited to the aforementioned one. For example, after fixing frame 14 on substrate 11, metal film 12 and reaction sites may be formed.

(Detection Method of Analyte)

In the following, a detection method of an analyte using detection chip 10 according to the embodiment will be described. For example, an analyte can be detected using detection apparatus (SPFS apparatus) 100 described hereinafter.

Figure 4:
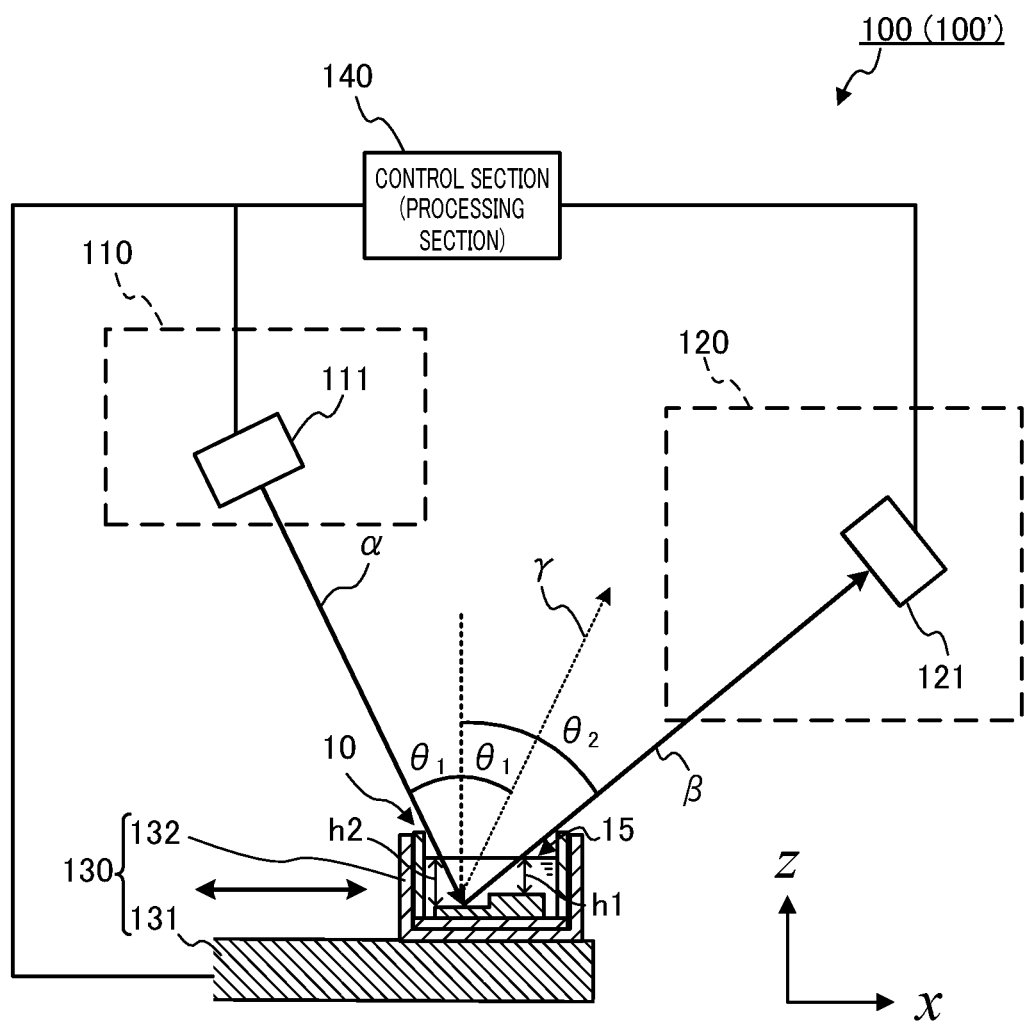
FIG. 4 is a schematic view illustrating a configuration of a SPFS apparatus.

FIG. 4 is a schematic view illustrating a configuration of detection apparatus (SPFS apparatus) 100 for detecting an analyte using detection chip 10. The configuration of SPFS apparatus 100 will be described first, followed by the description of a detection method of an analyte using detection chip 10 and SPFS apparatus 100.

As illustrated in FIG. 4, SPFS apparatus 100 includes excitation light irradiation section 110, fluorescence detection section 120, conveyance section 130, and control section 140. Detection chip 10 is used while being mounted on chip holder 132 of SPFS apparatus 100.

Excitation light irradiation section 110 irradiates metal film 12 (diffraction grating 13) of detection chip 10 with excitation light α having a certain wavelength and quantity of light. In this step, excitation light irradiation section 110 irradiates metal film 12 (diffraction grating 13) with p-polarized light relative to a surface of metal film 12 so as to generate diffracted light that can couple with surface plasmon in metal film 12. The optical axis of excitation light α extends along the alignment direction of a periodic structure of diffraction grating 13 (x-axis direction in FIG. 4). Accordingly, the optical axis of excitation light α is parallel to xz-plane (see FIG. 4). Since excitation light α is p-polarized light relative to a surface of metal film 12, the oscillation direction of the electric field of excitation light α is parallel to xz-plane including the optical axis of excitation light α and a normal line to a surface of metal film 12.

Excitation light irradiation section 110 includes at least light source 111. Excitation light irradiation section 110 may further include a collimator lens, an excitation light filter, and/or the like. Light source 111 emits excitation light α toward diffraction grating 13 of detection chip 10. The types of light source 111 are not limited. Examples of the types of light source 111 include a light emitting diode, a mercury lamp, and other laser light sources. In the embodiment, light source 111 is a laser diode. The wavelength of excitation light α emitted from light source 111 is, for example, in a range of 400 nm to 1,000 nm. The size of an irradiation spot is preferably about 1 mm ø, for example.

Incident angle $\theta_1$ of excitation light α on metal film 12 (see FIG. 4) is preferably an angle in which the intensity of enhanced electric fields generated by SPR is highest, and consequently the intensity of fluorescence β from a fluorescent substance is also highest. Incident angle $\theta_1$ of excitation light α is appropriately selected in accordance with a pitch of grooves of diffraction grating 13, a wavelength of excitation light α, the type of component metal of metal film 12, and/or the like. Since an optimal incident angle $\theta_1$ of excitation light α varies in accordance with changes in various conditions, SPFS apparatus 100 preferably includes a first angle adjustment section (not shown) configured to adjust incident angle $\theta_1$ by relatively rotating the optical axis of excitation light α and detection chip 10. The first angle adjustment section, for example, may rotate excitation light irradiation section 110 or detection chip 10 around the intersection between the optical axis of excitation light α and metal film 12.

As illustrated in FIG. 4, excitation light irradiation section 110 irradiates diffraction grating 13 (metal film 12) with excitation light α at a specific incident angle $\theta_1$. In the irradiated region, surface plasmon generated in metal film 12 and evanescent waves generated by diffraction grating 13 are coupled, thereby generating SPR. When a fluorescent substance is present in the irradiated region, the fluorescent substance is excited by enhanced electric fields generated by SPR, and thus fluorescence β is emitted. As described above, in GC-SPFS, different from PC-SPFS, fluorescence β is emitted with directivity in a particular direction. For example, emission angle $\theta_2$ of fluorescence β is approximated by $2\theta_1$. Under conditions for generating SPR, reflected light γ of excitation light α scarcely occurs.

Fluorescence detection section 120 detects at least twice fluorescence β emitted from a fluorescent substance above metal film 12 (diffraction grating 13). More specifically, fluorescence detection section 120 detects at least once fluorescence β emitted from a fluorescent substance above first reaction site 17 while the depth of a liquid above first reaction site 17 is first depth h1, and detects at least once fluorescence β emitted from a fluorescent substance above second reaction site 18 while the depth of a liquid above second reaction site 18 is second depth h2. Fluorescence detection section 120 is disposed so as to sandwich a normal line to the surface of metal film 12, which passes through the intersection between the optical axis of excitation light α and metal film 12, between fluorescence detection section 120 and excitation light irradiation section 110.

Fluorescence detection section 120 includes at least light receiving sensor 121. Fluorescence detection section 120 may further include a condensing lens group, an aperture stop, a fluorescence filter, or the like. Light receiving sensor 121 detects fluorescence β emitted from a fluorescent substance present above metal film 12, and thus detects a fluorescence image above metal film 12. The type of light receiving sensor 121, although not limited, is a photomultiplier tube with high sensitivity and S/N ratio, for example, and may be an avalanche photodiode (APD), a photodiode (PD), a CCD image sensor, or the like.

In GC-SPFS, fluorescence β from a fluorescent substance immobilized above metal film 12 is found to be emitted with directivity in a particular direction from diffraction grating 13 (reaction site). In this case, an angle of the optical axis of fluorescence detection section 120 from the normal line (to the surface of metal film 12) is preferably an angle with maximum intensity of fluorescence β (fluorescence peak angle). Accordingly, SPFS apparatus 100 preferably includes a second angle adjustment section (not shown) configured to adjust an angle of the optical axis of fluorescence detection section 120 by relatively rotating the optical axis of fluorescence detection section 120 and detection chip 10. For example, the second angle adjustment section may rotate fluorescence detection section 120 or detection chip 10 around the intersection between the optical axis of fluorescence detection section 120 and metal film 120.

Conveyance section 130 moves a position of detection chip 10. Conveyance section 130 includes conveyance stage 131 and chip holder 132. Chip holder 132 is fixed to conveyance stage 131 and holds detection chip 10 detachably. The shape of chip holder 132 is a shape that can holds detection chip 10 without obstructing the optical paths of excitation light α and fluorescence β. Conveyance stage 131 moves chip holder 132 in one direction and in the opposite direction. The shape of conveyance stage 131 is also a shape without obstructing the optical paths of excitation light α and fluorescence β. Conveyance stage 131 is driven by a stepping motor and/or the like, for example.

Control section 140 controls the operation of excitation light irradiation section 110 (light source 111 and first angle adjustment section), fluorescence detection section 120 (light receiving sensor 121 and second angle adjustment section), and conveyance section 130 (conveyance stage 131). Also, control section 140 functions as a processing section for processing output signals (detected results) from fluorescence detection section 120. Specifically, the processing section calculates, based on two or more detected values at fluorescence detection section 120 (light receiving sensor 121), a signal value indicating the presence or an amount of an analyte and a noise value as needed. Control section 140 is, for example, a computer that includes an arithmetic apparatus, a control apparatus, a storage apparatus, an input apparatus, and an output apparatus, and executes software.

(Detection Operation at SPFS Apparatus)

Figure 5:
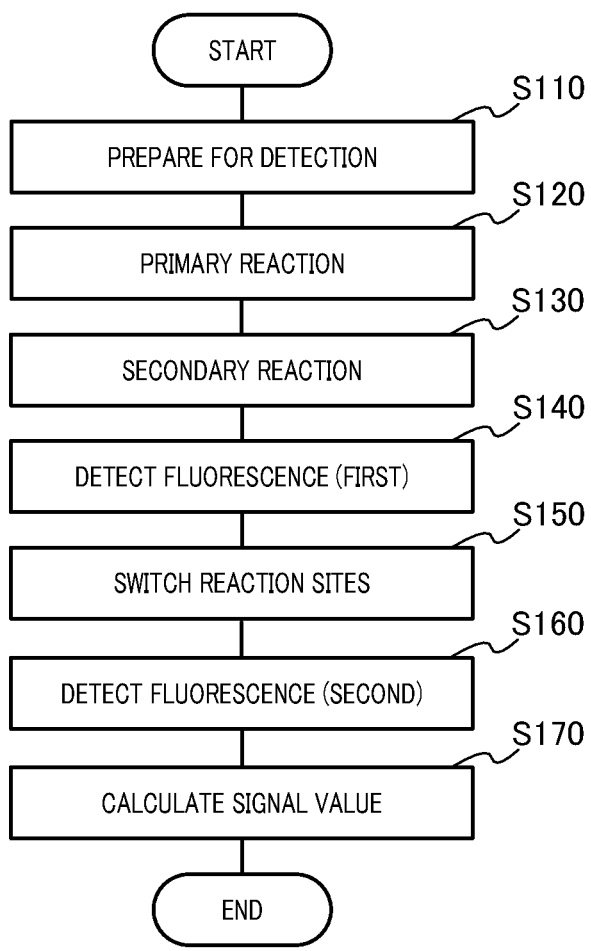
FIG. 5 is a flow chart showing an example of an operational procedure of a SPFS apparatus.

In the following, the detection operation of SPFS apparatus 100 (detection method according to the embodiment) will be described. FIG. 5 is a flow chart illustrating an example of an operational procedure of SPFS apparatus 100. Described will be an example in which a primary antibody is used as ligand 16, and an analyte is labeled with a fluorescent substance by binding a secondary antibody labeled with the fluorescent substance to the analyte captured by the primary antibody.

First, the detection is prepared (step S 110). Specifically, detection chip 10 is prepared, and then detection chip 10 is installed in chip holder 132 of SPFS apparatus 100. When a humectant is present above metal film 12 of detection chip 10, the humectant is removed by washing above metal film 12 so that a primary antibody captures an analyte properly.

Then, the analyte in a sample and the primary antibody are bound to each other (primary reaction: step S 120). Specifically, the sample is provided to above metal film 12 so that the sample comes into contact with the primary antibody. When an analyte is present in the sample, at least part of the analyte binds to the primary antibody.

Then, the analyte bound to the primary antibody is labeled with a fluorescent substance (secondary reaction: step S 130). Specifically, a fluorescent labeling solution containing a secondary antibody labeled with a fluorescent substance is provided to above metal film 12 so that the analyte bound to the primary antibody comes into contact with the fluorescent labeling solution. The fluorescent labeling solution is a buffer containing a secondary antibody labeled with a fluorescent substance, for example. When an analyte is bound to a primary antibody, at least part of the analyte is labeled with a fluorescent substance. In this case, a liquid (e.g., buffer or fluorescent labeling solution) is housed in first depth h1 above first reaction site 17 and in second depth h2 above second reaction site 18. As described hereinafter, SPFS apparatus 100 according to the embodiment can detect an analyte even without removal of a free secondary antibody. It is preferable, however, to wash above metal film 12 with a buffer or the like after labeling with a fluorescent substance to remove a free secondary antibody.

The order of the primary reaction and the secondary reaction is not limited to the aforementioned one. For example, after binding an analyte to a secondary antibody, a liquid containing the complex may be provided to above metal film 12. Alternatively, a sample and a fluorescent labeling solution may be provided to above metal film 12 simultaneously.

Then, fluorescence β emitted from the fluorescent substance above first reaction site 17 (metal film 12) is detected while diffraction grating 13 (metal film 12) positioned under first reaction site 17 is irradiated with excitation light α (step S 140). Specifically, control section 140 operates excitation light irradiation section 110 to irradiate diffraction grating 13 where first reaction site 17 is disposed with excitation light α so as to generate SPR, and simultaneously records detected value $I_a$ at light receiving sensor 121. During this operation, a liquid is housed in first depth h1 above first reaction site 17.

Then, reaction sites as detection targets are switched (step S 150). Specifically, control section 140 operates conveyance stage 131 to move detection chip 10. This enables excitation light irradiation section 110 to irradiate second reaction site 18 with excitation light α.

Then, fluorescence β emitted from the fluorescent substance above second reaction site 18 (metal film 12) is detected while diffraction grating 13 (metal film 12) positioned under second reaction site 18 is irradiated with excitation light α (step S 160). Specifically, control section 140 operates excitation light irradiation section 110 to irradiate diffraction grating 13 where second reaction site 18 is disposed with excitation light α so as to generate SPR, and simultaneously records output value $I_b$ at light receiving sensor 121. During this operation, a liquid is housed in second depth h2 above second reaction site 18.

Even when inside housing section 15 is washed by replacing the fluorescent labeling solution inside housing section 15 with a secondary antibody-free buffer after the secondary reaction (step S 130), part of the secondary antibody bound to the analyte is released in the buffer. Alternatively, when washing is not performed after the secondary reaction (step S 130), the fluorescent labeling solution is left untouched inside housing section 15. Accordingly, in either the cases, detected value $I_a$ in step S 140 and detected value $I_b$ in step S 160 contain a fluorescence β component emitted from the fluorescent substance (mainly the fluorescent substance labeling the analyte captured by the primary antibody), which is excited by enhanced electric fields due to SPR, and a fluorescence β component emitted from the fluorescent substance (mainly the free fluorescent substance in the liquid inside housing section 15), which is excited by light other than that excited by enhanced electric fields due to SPR (excitation light α and extraneous light).

Finally, control section (processing section) 140 calculates a signal value indicating the presence or an amount of the analyte based on detected values obtained at fluorescence detection section 120 in steps S 140 to S 160 (step S 170). A calculation method of the signal value will be described hereinafter.

Figure 6A:
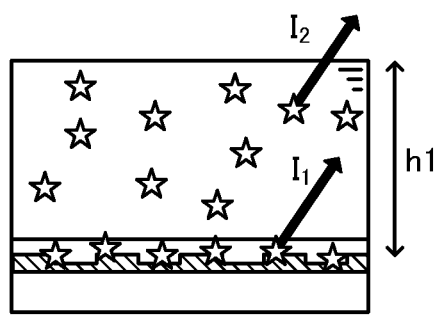
FIG. 6A and FIG. 6B are schematic views for explaining a detection principle of an analyte at a SPFS apparatus.
Figure 6B:
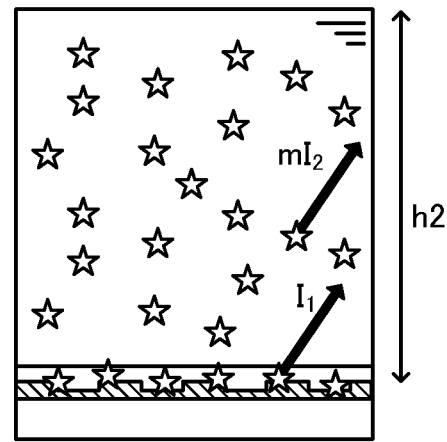

FIGS. 6A and 6B are schematic views for explaining a detection principle of an analyte at SPFS apparatus 100. FIG. 6A illustrates a state in which a liquid is present in first depth h1 above first reaction site 17, and FIG. 6B illustrates a state in which a liquid is present in second depth h2 above second reaction site 18. In FIGS. 6A and 6B, white stars represent a fluorescent substance.

As illustrated in FIG. 6A, in a state in which a liquid is present in first depth h1, fluorescence β emitted from first reaction site 17 contains light generated while being influenced by enhanced electric fields due to SPR and light generated without being influenced by enhanced electric fields due to SPR. In other words, a detected value during the detection of fluorescence β contains component $I_1$ of light generated while being influenced by enhanced electric fields due to SPR (signal component) and component $I_2$ of light generated without being influenced by enhanced electric fields due to SPR (noise component). In this case, $I_1$ is mainly attributed to fluorescence β from a fluorescent substance that labels an analyte captured by a primary antibody, and $I_2$ is mainly attributed to fluorescence β from a free fluorescent substance in a liquid inside housing section 15. Accordingly, $I_1$ is a signal value indicating the presence or an amount of an analyte, and $I_2$ is a noise value. Therefore, in a state in which the depth of a liquid above first reaction site 17 is first depth h1, detected value $I_a$ at fluorescence detection section 120 is represented by the following equation 1.

[1]

$$I_1 + I_2 = I_a \quad \text{(Equation 1)}$$

Further, as illustrated in FIG. 6B, in a state in which a liquid is present in second depth h2, fluorescence β emitted from second reaction site 18 contains light generated while being influenced by enhanced electric fields due to SPR and light generated without being influenced by enhanced electric fields due to SPR. Meanwhile, a distance from a surface of diffraction grating 13 where the effects of enhanced electric fields due to SPR are exerted is constant regardless of the depth of a liquid housed inside housing section 15. Thus, the magnitude of $I_1$ is the same both in a state in which a liquid is present in first depth h1 and in a state in which a liquid is present in second depth h2.

Meanwhile, when a ratio of second depth h2 to first depth h1 is m, present above reaction site 18 are a liquid in a volume m times a volume above first reaction site 17, and a fluorescent substance in an amount m times an amount above first reaction site 17. Compared with the depth of a liquid (several μm to several cm), a distance where the effects of enhanced electric fields are exerted, which is 100 nm or less, is small enough to be ignored. Accordingly, m can be approximated as a height ratio of a region of a liquid in depth h2 without being influenced by enhanced electric fields due to SPR to a region of a liquid in depth h1 without being influenced by enhanced electric fields due to SPR. Thus, fluorescence β emitted while a liquid is present in second depth h2 contains m times $I_2$ contained in fluorescence β emitted while a liquid is present in first depth h1. Therefore, in a state in which the depth of a liquid above second reaction site 18 is second depth h2 in step S 160, detected value $I_b$ at fluorescence detection section 120 is represented by the following equation 2.

[2]

$$I_1 + m \times I_2 = I_b \quad \text{(Equation 2)}$$

Control section (processing section) 140 calculates $I_1$ represented by the following equation 3 as a signal value indicating the presence or an amount of an analyte based on detected values $I_a$ and $I_b$ represented by equation 1 and equation 2, respectively.

(Equation 3)

$$I_1 = \frac{m \times I_a - I_b}{m - 1} \quad [3]$$

Moreover, control section (processing section) 140 can further calculate, as needed, noise value $I_2$ represented by the following equation 4, which indicates neither the presence nor an amount of an analyte.

(Equation 4)

$$I_2 = \frac{I_b - I_a}{m - 1} \quad [4]$$

Through the above procedure, the presence or an amount of an analyte in a sample can be detected. In the present invention, measurements of blank values may not necessarily be performed since noise can be eliminated through the above procedure.

(Advantageous Effects)

As described above, by using detection chip 10 according to the embodiment, background noise can be eliminated, and the presence or an amount of an analyte can be detected highly sensitively, easily, and accurately even if an unreacted fluorescent substance is present above metal film 12.

In addition, since the detection method according to the embodiment can eliminate noise component contained in fluorescence β, an analyte can be detected without removal of a free secondary antibody after performing the secondary reaction (step S 130).

In the embodiment, the order of the first detection step of fluorescence β (step S 140) and the second detection step of fluorescence β (step S 160) is not limited to the aforementioned one. In other words, fluorescence β emitted from above first reaction site 17 may be detected after detecting fluorescence β emitted from above second reaction site 18.

Figure 7A:
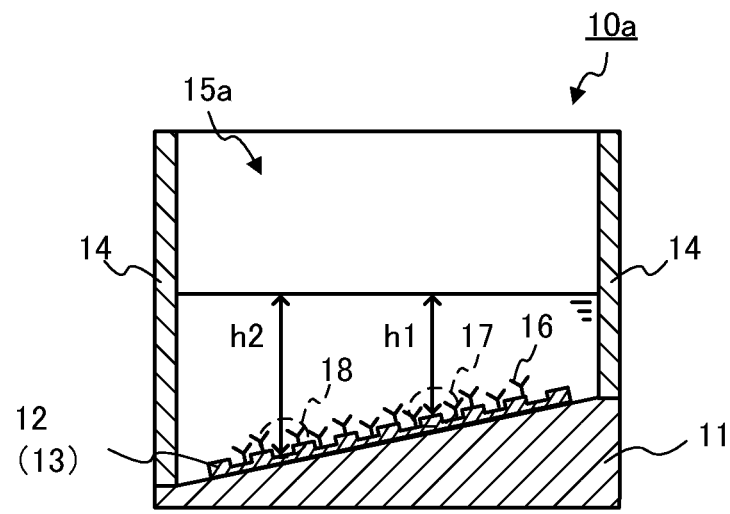
FIG. 7A is a sectional view illustrating a configuration of a detection chip according to Modification 1.
Figure 7B:
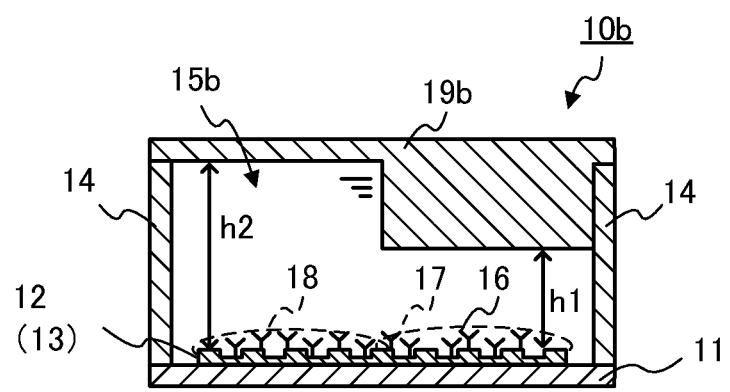
FIG. 7B is a sectional view illustrating a configuration of a detection chip according to Modification 2.
Figure 7C:
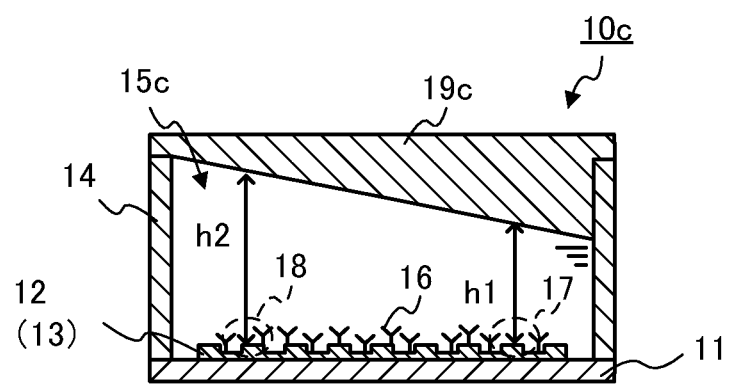
FIG. 7C is a sectional view illustrating a configuration of a detection chip according to Modification 3.

Detection chip 10, whose housing section 15 has a first bottom surface and a second bottom surface, is described in the embodiment. The detection chip according to the present invention, however, is not limited to this mode, and may be detection chip 10a, 10b, or 10c illustrated in FIGS. 7A to 7C, for example. FIG. 7A is a sectional view illustrating a configuration of detection chip 10a according to Modification 1, FIG. 7B is a sectional view illustrating a configuration of detection chip 10b according to Modification 2, and FIG. 7C is a sectional view illustrating a configuration of detection chip 10c according to Modification 3.

As illustrated in FIG. 7A, in detection chip 10a according to Modification 1, a bottom surface of housing section 15a contains a sloping surface. Thus, in detection chip 10a, first reaction site 17 and second reaction site 18 are disposed in predetermined different regions on the sloping surface. Also, as illustrated in FIG. 7B, detection chip 10b according to Modification 2 further includes lid 19b to be disposed in the upper portion of housing section 15b. The shape of lid 19b is not limited as long as a liquid can be housed in first depth h1 and in second depth h2 inside housing section 15. In the embodiment, lid 19b has a step. Because of this, when lid 19b is disposed on frame 14, housing section 15b includes a first upper surface and a second upper surface each disposed at a different height. In this case, first reaction site 17 is disposed on metal film 12 in a position facing the first upper surface, and second reaction site 18 is disposed on metal film 12 in a position facing the second upper surface. Further, as illustrated in FIG. 7C, detection chip 10c according to Modification 3 further includes lid 19c, which is disposed in the upper portion of housing section 15c and contains a sloping surface relative to a bottom surface of housing section 15c. In detection chip 10c, first reaction site 17 and second reaction site 18 are disposed in predetermined different regions on metal film 12 in positions facing the sloping surface. Any detection chip 10a, 10b, or 10c can be used in the same manner as detection chip 10.

As detection chips 10b and 10c according to Modifications 2 and 3, the detection chip according to the present invention may have a lid. The lid may preferably be formed from a material transparent to excitation light $\alpha$ and fluorescence $\beta$. Examples of the materials for the lid include resins. As long as a portion where excitation light $\alpha$ and fluorescence $\beta$ pass through is transparent to excitation light $\alpha$ and fluorescence $\beta$, the other portion of the lid may be formed from opaque materials. The lid is joined with a frame through, for example, bonding with a double-stick tape, an adhesive, or the like, laser welding, ultrasonic welding, or crimping with a clamping member.

Further, although detection chip 10 according to the embodiment and detection chip 10b according to Modification 2 have two terrace surfaces on the bottom or the upper surface of housing section 15, the number of terrace surfaces is not limited to this, and may be three or more, for example.

[Embodiment 2]

Detection chip 10' according to Embodiment 2 has the same configuration as that of detection chip 10 according to Embodiment 1, and SPFS apparatus 100' using detection chip 10' according to Embodiment 2 also has the same configuration as that of SPFS apparatus 100 according to Embodiment 1. Meanwhile, the detection method according to Embodiment 2 is different from the detection method according to Embodiment 1 in that the former performs real-time measurements. Accordingly, the description of the configurations of detection chip 10' and SPFS apparatus 100' is omitted, and only an operational procedure of SPFS apparatus 100' will be described.

SPFS apparatus 100' according to the embodiment continually irradiates diffraction grating 13 positioned under first reaction site 17 and second reaction site 18 with excitation light $\alpha$, and continually detects fluorescence $\beta$ emitted from a fluorescent substance. The term "continual" herein refers to not only continuous operation, but also intermittent operation. Accordingly, the phrase "continual irradiation with excitation light" means irradiation with excitation light $\alpha$ for proper time at proper frequency that allows detection of changes in analyte over time. The phrase "continual detection of fluorescence" herein means detection of fluorescence $\beta$ for proper time at proper frequency that allows detection of changes in analyte over time.

For example, continual irradiation with excitation light $\alpha$ may be continuous irradiation with excitation light $\alpha$ or may be intermittent irradiation with excitation light $\alpha$. From the viewpoint of preventing fading of a fluorescent substance, continual irradiation with excitation light $\alpha$ is preferably intermittent irradiation with excitation light $\alpha$. In this case, an interval for irradiation with excitation light $\alpha$ may be constant or inconstant (predetermined). Alternatively, an interval for irradiation with excitation light $\alpha$ may be automatically determined based on certain conditions, such as automatic calculation by a program, may be empirically determined by a preliminary experiment or the like, or may be predetermined by a user.

Also, an interval for irradiation with excitation light $\alpha$ may be determined in accordance with detected results of fluorescence intensity. For example, when a detected value of fluorescence intensity is small, an interval for irradiation with excitation light $\alpha$ may be shortened further, whereas when a detected value of fluorescence intensity is large, an interval for irradiation with excitation light $\alpha$ may be extended further. Alternatively, when a detected value of fluorescence intensity largely varies over time, an interval for irradiation with excitation light $\alpha$ may be shortened further, whereas when a detected value of fluorescence intensity slightly varies over time, an interval for irradiation with excitation light $\alpha$ may be extended further. Such adjustment of an interval for irradiation with excitation light $\alpha$ can be performed by, for example, appropriate setting of a threshold value for detected values of fluorescence intensity, and feedback control based on detected values of fluorescence intensity. From the viewpoint of closely observing changes in analyte over time, such adjustment of an interval for irradiation with excitation light $\alpha$ is preferable.

The same applies to the timing of continual detection of fluorescence $\beta$.

Figure 8:
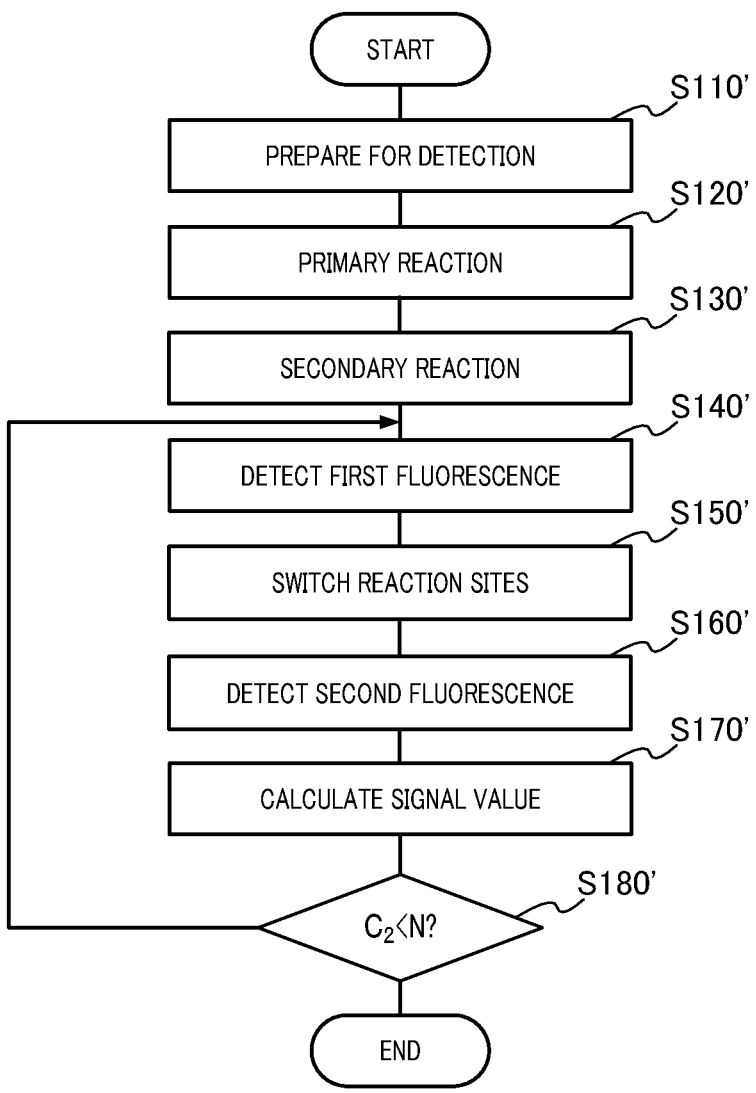
FIG. 8 is a flow chart showing another example of an operational procedure of a SPFS apparatus.

FIG. 8 is a flow chart showing an example of an operational procedure of SPFS apparatus 100' according to Embodiment 2. In this example, a primary antibody as a ligand is immobilized above metal film 12. As a ligand for fluorescent labeling, a secondary antibody labeled with a fluorescent substance is used.

First, the detection is prepared (step S 110'). Specifically, detection chip 10' is prepared, and then detection chip 10' is installed in chip holder 132 of SPFS apparatus 100'. In the same manner as Embodiment 1, above metal film 12 is washed as needed.

Then, an analyte in a sample is reacted with a primary antibody (primary reaction: step S 120'). Specifically, a sample is provided to above metal film 12 so that the sample comes into contact with the primary antibody. When an analyte is present in the sample, at least part of the analyte binds to the primary antibody. After that, above metal film 12 is washed with a buffer or the like to remove a substance unbound to the primary antibody.

Then, the analyte bound to the primary antibody is labeled with a fluorescent substance (secondary reaction: step S 130'). Specifically, a fluorescent labeling solution containing a secondary antibody labeled with a fluorescent substance is provided to above metal film 12 so that the analyte bound to the primary antibody comes into contact with the fluorescent labeling solution. The fluorescent labeling solution is, for example, a buffer containing a secondary antibody labeled with a fluorescent substance. When an analyte is bound to a primary antibody, at least part of the analyte is labeled with the fluorescent substance. In the same manner as Embodiment 1, SPFS apparatus 100' can measure an analyte without removal of a free secondary antibody. In this case, a liquid (e.g., buffer or fluorescent labeling solution) is housed in first depth h1 above first reaction site 17 and in second depth h2 above second reaction site 18.

The order of the primary reaction and the secondary reaction is not limited to the aforementioned one. For example, after binding an analyte to a secondary antibody, a liquid containing the complex may be provided to above metal film 12. Alternatively, a sample and a fluorescent labeling solution may be provided to above metal film 12 simultaneously.

Then, fluorescence $\beta$ emitted from the fluorescent substance above first reaction site 17 (metal film 12) is detected while metal film 12 positioned under first reaction site 17 is irradiated with excitation light α (step S 140'), detection chip 10' is moved so that excitation light irradiation section 110 irradiates metal film 12 positioned under second reaction site 18 with excitation light α (step S 150'), fluorescence β emitted from the fluorescent substance above second reaction site 18 (metal film 12) is detected while metal film 12 positioned under second reaction site 18 is irradiated with excitation light α (step S 160'), and a signal value indicating the presence or an amount of the analyte is calculated based on results of fluorescence detection in steps S 140' and S 150' (step S 170'). These steps S 140' to S 170' as one cycle are repeated specific times (step S 180'). Through this step, fluorescence β emitted from the fluorescent substance present above first reaction site 17 while a liquid is present in first depth h1, and fluorescence β emitted from a fluorescent substance present above second reaction site 18 while a liquid is present in second depth h2 are alternately detected a plurality of times, thereby obtaining respective detected values $I_a$ and $I_b$ at fluorescence detection section 120 continually (intermittently) while calculating signal values indicating the presence or an amount of the analyte continually (intermittently).

Specifically, in step S140', control section 140 operates light source 111 to emit excitation light α continuously or intermittently at a specific interval (i.e., "continually"). The phrase "at a specific interval" herein refers to, for example, an interval for switching reaction sites as a detection target described hereinafter. At the same time, control section 140 operates fluorescence detection section 120 to detect fluorescence β emitted from the fluorescent substance present above metal film 12 continually. The timing of the continual detection of fluorescence β may be synchronized with or different from the timing of irradiation with excitation light α over time.

As described in Embodiment 1, fluorescence β emitted from above first reaction site 17 while a liquid is present in first depth h1 contains light generated while being influenced by enhanced electric fields due to SPR and light generated without being influenced by enhanced electric fields due to SPR. In other words, detected value $I_a$ during the detection of fluorescence β contains component $I_1$ of light generated while being influenced by enhanced electric fields due to SPR (signal component) and component $I_2$ of light generated without being influenced by enhanced electric fields due to SPR (noise component) (see FIG. 6A). Therefore, in step 140' in a state in which the depth of a liquid above first reaction site 17 is first depth h1, detected value $I_a$ at fluorescence detection section 120 is represented by the following equation 5.

[5]

$$I_1 + I_2 = I_a \quad \text{(Equation 5)}$$

In step 160', control section 140 operates light source 111 to keep emitting excitation light α continually. At the same time, control section 140 operates fluorescence detection section 120 to detect fluorescence β from metal film 12 continually.

As described in Embodiment 1, fluorescence β emitted from second reaction site 18 while a liquid is present in second depth h2 also contains light generated while being influenced by enhanced electric fields due to SPR and light generated without being influenced by enhanced electric fields due to SPR. In other words, detected value $I_b$ during the detection of fluorescence β contains component $I_1$ of light generated while being influenced by enhanced electric fields due to SPR (signal component) and component $I_2$ of light generated without being influenced by enhanced electric fields due to SPR (noise component) (see FIG. 6B). Also in Embodiment 2, noise component $I_2$ in detection of fluorescence β while a liquid is presence in second depth h2 contains noise component m (h2/h1) times noise component in detection of fluorescence β while a liquid is present in first depth h1. Therefore, in step S 160' in a state in which the depth of a liquid above second reaction site 18 is second depth h2, detected value $I_b$ at fluorescence detection section 120 is represented by the following equation 6.

[6]

$$I_1 + m \times I_2 = I_b \quad \text{(Equation 6)}$$

The order of the first fluorescence detection (step S 140') and the second fluorescence detection (step S 160') is not limited to the aforementioned one. In other words, the detection of fluorescence β emitted from above first reaction site 17 (first fluorescence detection) may be performed after the detection of fluorescence β emitted from above second reaction site 18 (second fluorescence detection).

In step S 170', control section (processing section) 140 calculates signal value which is represented by the following equation 7, and indicates the presence or an amount of the analyte based on detected values $I_a$ and $I_b$ obtained at fluorescence detection section 120 represented by equation 5 and equation 6, respectively (step S 180'). Noise value $I_2$ can be calculated as needed.

(Equation 7)

$$I_1 = \frac{m \times I_a - I_b}{m - 1} \quad [7]$$

in which m is a ratio of the second depth h2 to the first depth h1, and is a real number excluding 1.

In step S 180', for example, control section 140 counts the number of the second detection of fluorescence β ($C_2$), adjusts so that first reaction site 17 becomes a detection target again when $C_2$ does not reach a set value (e.g., N times), and performs the first detection of fluorescence β by returning to step S 140'. When $C_2$ reaches N times, the detection is terminated.

Although the step of calculating a signal value (step S 170') is performed every time when the fluorescence detection (step S 140' and S 160') is performed, the step is not limited to this. For example, a signal value may be calculated after $C_2$ reaches N times and the detection of fluorescence β is terminated.

Thus, signal values that vary over time can be calculated in real time.

[Advantageous Effects]

As described above, even if an unreacted fluorescent substance is present above metal film 12, by using detection chip 10' according to the embodiment, background noise can be eliminated, and the presence or an amount of an analyte can be detected in real time. Therefore, in the detection of an analyte, real-time measurements can be performed highly sensitively, easily, and accurately by using detection chip 10' according to the embodiment.

Moreover, since SPFS apparatus 100' can eliminate noise component contained in fluorescence β, an analyte can be detected without removal of a free secondary antibody after performing the secondary reaction (step S 130').

Therefore, according to the detection method of each aforementioned embodiment, an analyte in an unpurified sample, such as a crude product in biosynthesis of a novel biomolecule or a raw sample collected in a clinical test, can be detected easily and highly accurately over time.

Although a mode without measurements of blank values is described in each aforementioned embodiment, blank values may be measured as needed before the secondary reaction (step S 130 or S 130'). In this case, specifically, blank values $I_a'$ and $I_b'$ are obtained in advance through the same procedure as in steps S 140 to S 160 or S 140' to S 160' while a fluorescent substance is absent in a liquid inside housing section 15. In this case, according to the aforementioned calculation method, signal value $I_1$ and noise value $I_2$, as needed, are calculated in step S 170 or S 170' after blank values $I_a'$ and $I_b'$ are subtracted from respective detected values $I_a$ and $I_b$.

Although the detection method utilizing GC-SPFS is described in each aforementioned embodiment, the detection method according to the embodiment may also utilize PC-SPFS. In this case, a detection chip includes a prism formed from a dielectric, and metal film 12 is disposed on the prism instead of substrate 11. In addition, metal film 12 lacks diffraction grating 13. Further, a rear surface of metal film 12 corresponding to reaction sites (first reaction site 17 and second reaction site 18) is irradiated with excitation light α through the prism.

Although an example in which detection chip 10 or 10' is irradiated with excitation light α from the side of metal film 12 is described in the embodiment, detection chip 10 or 10' may be irradiated from the side of substrate 11.

Furthermore, detection chips 10a to 10c according to the modifications can be used for the detection method according to Embodiment 2 (real-time measurements).

This application is entitled to and claims the benefit of Japanese Patent Application No. 2014-249044, filed on Dec. 9, 2014, the disclosure of which including the specification, drawings and abstract is incorporated herein by reference in its entirety.

INDUSTRIAL APPLICABILITY

The detection chip and the detection method according to the present invention can detect an analyte highly reliably, and thus are useful for clinical tests, for example.

Moreover, the detection chip and the detection method according to the present invention can detect an analyte highly reliably even without washing a metal film surface after a labeling solution or the like is provided. Thus, the detection chip and the detection method according to the present invention are expected to shorten the detection time, as well as to contribute to development, widespread use, and advancement of a downscalable quantitative immunoassay apparatus and an extremely simple quantitative immunoassay system.

REFERENCE SIGNS LIST 10, 10a, 10b, 10c, 10' Detection chip
11 Substrate
12 Metal film
13 Diffraction grating
14 Frame
15, 15a, 15b, 15c Housing section
16 Ligand
17 First reaction site
18 Second reaction site
19b, 19c Lid
100, 100' Surface plasmon-field enhanced fluorescence spectroscopy apparatus (SPFS apparatus)
110 Excitation light irradiation section
111 Light source
120 Fluorescence detection section
121 Light receiving sensor
130 Conveyance section
131 Conveyance stage
132 Chip holder
140 Control section (Processing section)
h1 First depth
h2 Second depth
α Excitation light
β Fluorescence
γ Reflected light

The invention claimed is:

1. A detection chip for use in detecting an analyte utilizing surface plasmon resonance, the chip comprising:
    a housing section for housing a liquid;
    a metal film disposed in a bottom portion of the housing section so that one surface of the metal film faces inside the housing section;
    a first reaction site where a ligand for capturing an analyte is immobilized, the first reaction site being disposed on the one surface of the metal film; and
    a second reaction site where the ligand is immobilized, the second reaction site being disposed in a different region from the first reaction site on the one surface of the metal film, wherein
    when a liquid is housed inside the housing section, a depth of the liquid above the first reaction site is different from a depth of the liquid above the second reaction site, and irradiating the metal film with excitation light while liquid is present generates surface plasmon resonance and different amounts of detectable fluorescence above each of the first and second reaction sites.

2. The detection chip according to claim 1, wherein
    the housing section includes a first bottom surface and a second bottom surface disposed at a different height from a height of the first bottom surface,
    the first reaction site is disposed on the metal film above the first bottom surface, and
    the second reaction site is disposed on the metal film above the second bottom surface.

3. The detection chip according to claim 1, wherein
    the housing section includes a first upper surface and a second upper surface disposed at a different height from a height of the first upper surface,
    the first reaction site is disposed on the metal film in a position facing the first upper surface, and
    the second reaction site is disposed on the metal film in a position facing the second upper surface.

4. The detection chip according to claim 1, wherein
    a bottom surface of the housing section contains a sloping surface, and
    the first reaction site and the second reaction site are disposed on the metal film above the sloping surface.

5. The detection chip according to claim 1, wherein
    the housing section includes an upper surface containing a sloping surface relative to a bottom surface, and
    the first reaction site and the second reaction site are disposed on the metal film in a position facing the sloping surface.

6. The detection chip according to claim 1, wherein the metal film includes a diffraction grating in a region corresponding to the first reaction site and the second reaction site.

7. A detection method for detecting an analyte utilizing surface plasmon resonance, the method comprising:
- a first step of binding an analyte labeled with a fluorescent substance to the ligand in the first reaction site and in the second reaction site inside the housing section of the detection chip according to claim 6;
- a second step of irradiating the metal film positioned under the first reaction site with excitation light so as to generate surface plasmon resonance while the liquid is present inside the housing section in a first depth of the liquid above the first reaction site, and detecting fluorescence emitted from the fluorescent substance present above the first reaction site;
- a third step of irradiating the metal film positioned under the second reaction site with excitation light so as to generate surface plasmon resonance while the liquid is present inside the housing section in a second depth of the liquid different from the first depth above the second reaction site, and detecting fluorescence emitted from the fluorescent substance present above the second reaction site; and
- a fourth step of calculating a signal value which indicates the presence or an amount of an analyte based on a detected value obtained in each of the second step and the third step.

8. The detection method according to claim 7, wherein
in the second step and in the third step, the diffraction grating is irradiated with excitation light; and
in the fourth step, a signal value $I_i$ which is represented by the following equation 1 and indicates the presence or an amount of an analyte is calculated based on a detected value $I_a$ obtained in the second step and a detected value $I_b$ obtained in the third step:

(Equation 1)

$$I_1 = \frac{m \times I_a - I_b}{m - 1} \qquad [1]$$

wherein m is a ratio of the second depth to the first depth, and is a positive real number excluding 1.

9. The detection method according to claim 8, wherein
in the fourth step, a noise value $I_2$ originated from light which is contained in the fluorescence and generated without being influenced by an enhanced electric field due to the surface plasmon resonance is further calculated according to the following equation 3:

(Equation 3)

$$I_2 = \frac{I_b - I_a}{m - 1}. \qquad [3]$$

10. The detection chip according to claim 1, further comprising a prism formed from a dielectric, wherein the metal film is disposed on one surface of the prism which constitutes a bottom surface of the housing section.

11. A detection method for detecting an analyte utilizing surface plasmon resonance, the method comprising:
- a first step of binding an analyte labeled with a fluorescent substance to the ligand in the first reaction site and in the second reaction site inside the housing section of the detection chip according to claim 10;
- a second step of irradiating the metal film positioned under the first reaction site with excitation light so as to generate surface plasmon resonance while the liquid is present inside the housing section in a first depth of the liquid above the first reaction site, and detecting fluorescence emitted from the fluorescent substance present above the first reaction site;
- a third step of irradiating the metal film positioned under the second reaction site with excitation light so as to generate surface plasmon resonance while the liquid is present inside the housing section in a second depth of the liquid different from the first depth above the second reaction site, and detecting fluorescence emitted from the fluorescent substance present above the second reaction site; and
- a fourth step of calculating a signal value which indicates the presence or an amount of an analyte based on a detected value obtained in each of the second step and the third step.

12. The detection method according to claim 11, wherein
in the second step, a rear surface of the metal film corresponding to the first reaction site is irradiated with excitation light through the prism;
in the third step, a rear surface of the metal film corresponding to the second reaction site is irradiated with excitation light through the prism; and
in the fourth step, a signal value $I_i$ which is represented by the following equation 2 and indicates the presence or an amount of an analyte is calculated based on a detected value $I_a$ obtained in the second step and a detected value $I_b$ obtained in the third step:

(Equation 2)

$$I_1 = \frac{m \times I_a - I_b}{m - 1} \qquad [2]$$

wherein m is a ratio of the second depth to the first depth, and is a positive real number excluding 1.

13. The detection method according to claim 12, wherein
in the fourth step, a noise value $I_2$ originated from light which is contained in the fluorescence and generated without being influenced by an enhanced electric field due to the surface plasmon resonance is further calculated according to the following equation 3:

(Equation 3)

$$I_2 = \frac{I_b - I_a}{m - 1}. \qquad [3]$$

14. A detection method for detecting an analyte utilizing surface plasmon resonance, the method comprising:
- a first step of binding an analyte labeled with a fluorescent substance to the ligand in the first reaction site and in the second reaction site inside the housing section of the detection chip according to claim 1;
- a second step of irradiating the metal film positioned under the first reaction site with excitation light so as to generate surface plasmon resonance while the liquid is present inside the housing section in a first depth of the liquid above the first reaction site, and detecting fluorescence emitted from the fluorescent substance present above the first reaction site;

a third step of irradiating the metal film positioned under the second reaction site with excitation light so as to generate surface plasmon resonance while the liquid is present inside the housing section in a second depth of the liquid different from the first depth above the second reaction site, and detecting fluorescence emitted from the fluorescent substance present above the second reaction site; and a fourth step of calculating a signal value which indicates the presence or an amount of an analyte based on a detected value obtained in each of the second step and the third step.

15. The detection method according to claim 14, wherein
in the second step and in the third step, the fluorescence is detected continually; and
in the fourth step, the signal value is calculated continually based on a detected value obtained in each of the second step and the third step.

* * * * *